(12) United States Patent
Knight et al.

(10) Patent No.: US 8,923,478 B2
(45) Date of Patent: Dec. 30, 2014

(54) X-RAY INSPECTION APPARATUS FOR PIPELINE GIRTH WELD INSPECTION

(75) Inventors: Stephen Knight, Norfolk (GB); Stephen G. Drake, Norfolk (GB)

(73) Assignee: ShawCor Ltd., Toronto, Ontario (CA)

( * ) Notice: Subject to any disclaimer, the term of this patent is extended or adjusted under 35 U.S.C. 154(b) by 315 days.

(21) Appl. No.: 13/501,874

(22) PCT Filed: Oct. 12, 2010

(86) PCT No.: PCT/GB2010/001900
§ 371 (c)(1),
(2), (4) Date: Apr. 13, 2012

(87) PCT Pub. No.: WO2011/045563
PCT Pub. Date: Apr. 21, 2011

(65) Prior Publication Data
US 2012/0201348 A1 Aug. 9, 2012

(30) Foreign Application Priority Data

Oct. 13, 2009 (GB) .................................. 0917950.8

(51) Int. Cl.
G01V 5/14 (2006.01)
G01V 5/08 (2006.01)
G01V 5/04 (2006.01)
G01B 15/08 (2006.01)
G01N 23/18 (2006.01)
G01N 23/083 (2006.01)
H05G 1/02 (2006.01)

(52) U.S. Cl.
CPC .......... *G01N 23/18* (2013.01); *G01N 2223/628* (2013.01)
USPC ................ 378/60; 378/58; 378/59; 378/197; 378/198; 250/257; 250/266; 250/269.1

(58) Field of Classification Search
USPC ............. 378/58–60, 189, 193, 197, 198, 204, 378/205, 210; 250/253, 257, 261–268, 250/269.1, 269.2, 269.3, 522.1
See application file for complete search history.

(56) References Cited

U.S. PATENT DOCUMENTS 3,087,058 A * 4/1963 Arvanetakis et al. ........... 378/60
3,628,029 A * 12/1971 Tompkins ................ 250/363.01
(Continued)

FOREIGN PATENT DOCUMENTS

CN 1480301 6/1976
CN 1480301 A 3/2004
(Continued)

OTHER PUBLICATIONS

Notice of First Office Action (PCT Application in the National Phase), Application/Patent No. 201080046885.9, Applicant/Patentee: ShawCor Ltd., Title: X-Ray inspection Apparatus for Pipeline Girth Weld Inspection, The State Intellectual Property Office of The People's Republic of China, pp. 1-8.
(Continued)

*Primary Examiner* — Anastasia Midkiff
(74) *Attorney, Agent, or Firm* — DeLio, Peterson & Curcio, LLC

(57) ABSTRACT

An apparatus is provided for x-ray inspection of a pipeline girth weld. This comprises a directional x-ray source 5 which is insertable into a pipeline section and is rotatable within the pipeline. Means are provided to align the directional x-ray source with an external x-ray detector such that both may be rotated through 360 degrees substantially coaxially with the pipeline section. Means for sampling the data detected by the x-ray detector are provided so that it may be further analyzed.

23 Claims, 3 Drawing Sheets a, b, c, d,

(56) References Cited

U.S. PATENT DOCUMENTS

| | | | | |
|---|---|---|---|---|
| 3,665,187 | A | * | 5/1972 | Stein ................................ 378/60 |
| 3,683,186 | A | * | 8/1972 | Tompkins ........................ 378/55 |
| 3,691,385 | A | * | 9/1972 | Ketchbaw et al. .............. 378/60 |
| 3,904,878 | A | * | 9/1975 | Burch et al. .................... 378/60 |
| 3,949,227 | A | * | 4/1976 | Gambini et al. ................ 378/60 |
| 4,006,359 | A | * | 2/1977 | Sullins et al. ................... 378/60 |
| 4,061,199 | A | * | 12/1977 | Last ................................. 180/8.2 |
| 4,974,246 | A | | 11/1990 | Heiskel |
| 5,698,854 | A | | 12/1997 | Gupta |
| 7,508,910 | B2 | * | 3/2009 | Safai et al. ...................... 378/57 |
| 7,656,997 | B1 | | 2/2010 | Anjelly |
| 2003/0058991 | A1 | * | 3/2003 | Lott ................................. 378/60 |
| 2006/0198498 | A1 | * | 9/2006 | Birdwell et al. ............. 378/204 |

FOREIGN PATENT DOCUMENTS

| | | |
|---|---|---|
| CN | 201096731 | 8/2008 |
| GB | 915391 | 1/1963 |
| GB | 2105048 A | 3/1983 |
| RU | 2069854 | 11/1996 |
| RU | 2098796 | 12/1997 |
| RU | 2199109 | 2/2003 |

OTHER PUBLICATIONS

Decision to Grant—Application No. 2012112877/28(019354) Filing Date Oct. 12, 2010, Jun. 23, 2014, (English Version).
Decision to Grant—Application No. 2012112877/28(019354) Filing Date Oct. 12, 2010, Jun. 23, 2014, (Russian Version).

* cited by examiner d.

c.

b.

a.

X-RAY INSPECTION APPARATUS FOR PIPELINE GIRTH WELD INSPECTION

FIELD OF THE INVENTION

This invention relates to an x-ray inspection apparatus and method for pipeline girth weld inspection.

BACKGROUND OF THE INVENTION

It is well known in the art that pipeline girth (circumferential) welds are often inspected with radiography using a conventional x-ray crawler in conjunction with either x-ray film or real-time radiographic (RTR) detectors. These crawlers are used when access can be easily made to an open end of a pipeline section which is being welded to another pipeline section. The x-ray crawler comprises an x-ray source on a crawler or buggy which can be driven into the open end of the pipeline and which will crawl along the pipeline to the area of the circumferential weld.

The x-ray source is panoramic and mounted to be substantially central within the pipe and emits x-rays around a 360 degree arc around the weld surface. This type of x-ray source is generally used with x-ray film and is suitable for most pipe diameters.

Use of x-ray film requires time consuming and environmentally unfriendly chemical processing, washing and drying prior to the production of an image which can be viewed and stored.

RTR detectors may be used with a pipe center mounted panoramic x-ray source. However, their applications are typically limited to pipe diameters of 24 inches or less, as inspection times on larger diameters increase rapidly. This arises because as the pipe diameter increases, the intensity of x-ray flux at the weld falls off in accordance with the inverse square law as distance from the x-ray source increases. The result of this is that on medium to large diameter pipes, the x-ray flux is of such a reduced level that inspection with RTR detectors is unacceptably slow and therefore not commercially viable.

SUMMARY OF THE INVENTION

Preferred embodiments of the present invention provide a directional x-ray source, means for inserting the directional x-ray source into a pipeline section and for rotating the directional x-ray source through 360 degrees substantially coaxially with the pipeline section, whereby the directional x-ray source directs x-rays at the pipeline girth weld from a substantially constant distance around the weld, and an RTR detector system positioned externally of the pipeline weld.

The use of such an arrangement enables a cycle time of RTR weld inspection systems to be decreased, particularly on larger pipelines of, for example, 24 inches diameter or more because the x-ray source is closer to the RTR detector. Smaller diameter pipelines may also benefit from this invention.

By using this technique the x-ray intensity levels at the RTR detection system are increased significantly compared to a conventionally deployed panoramic x-ray source (e.g. by ten times on a 48 inch diameter pipe) and the effects of the inverse square or flux reduction with increased pipe diameter are eliminated. The scanning speed of the RTR detector at a constant wall thickness is related only to the pipeline circumference. This enables large diameter pipe circumferential welds to be rapidly inspected with a single RTR detector which scans around a weld in synchronism with an x-ray source on a suitable x-ray crawler.

BRIEF DESCRIPTION OF THE DRAWINGS

A preferred embodiment of the invention will now be described in detail, by way of example, with reference to the accompanying drawings in which.

DETAILED DESCRIPTION OF PREFERRED EMBODIMENT

Figure 1:
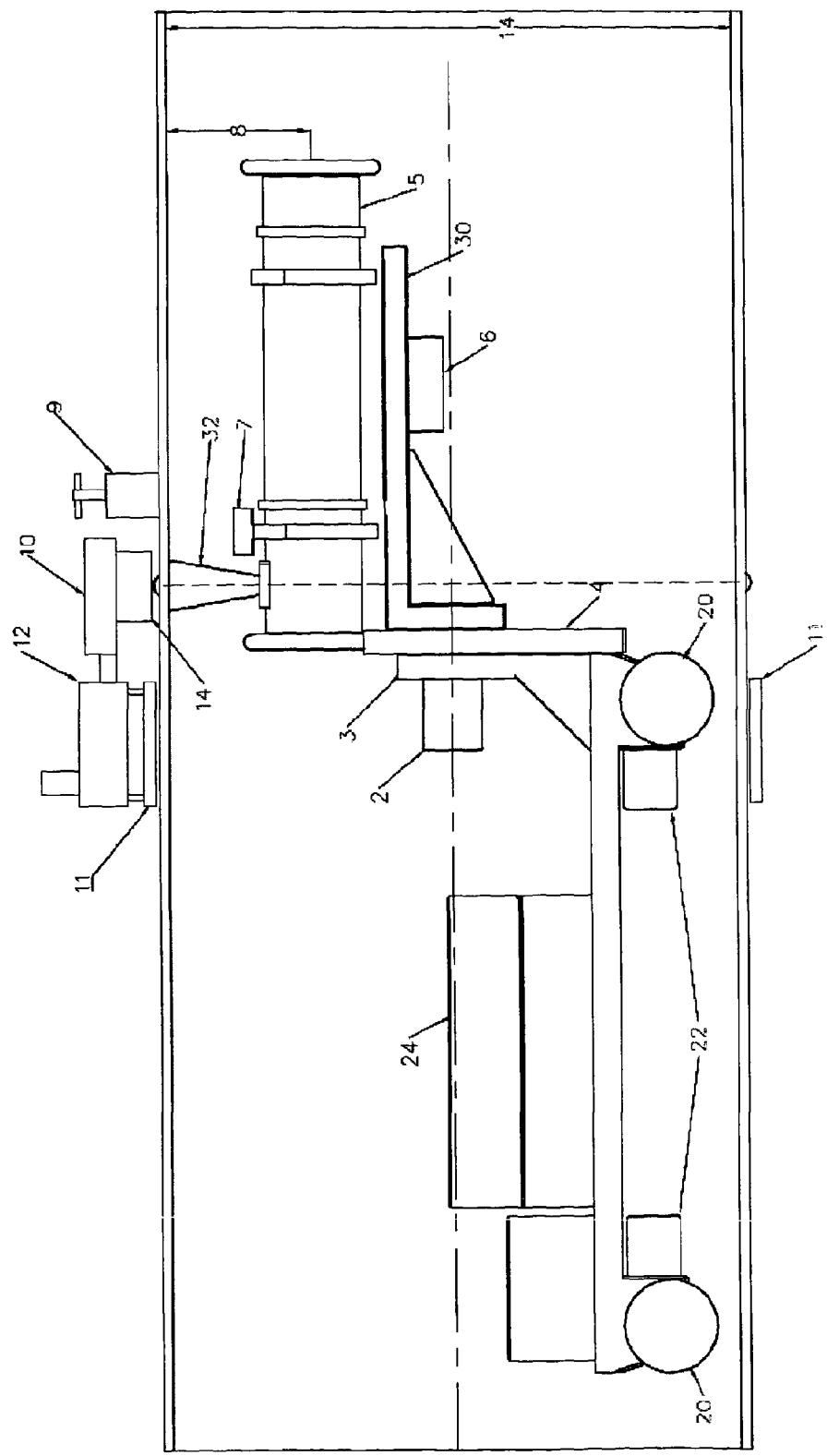
FIG. 1 shows a cross-section view through a pipeline in which an apparatus embodying the present invention is positioned with an x-ray detection system mounted externally to the pipeline.
Figure 2:
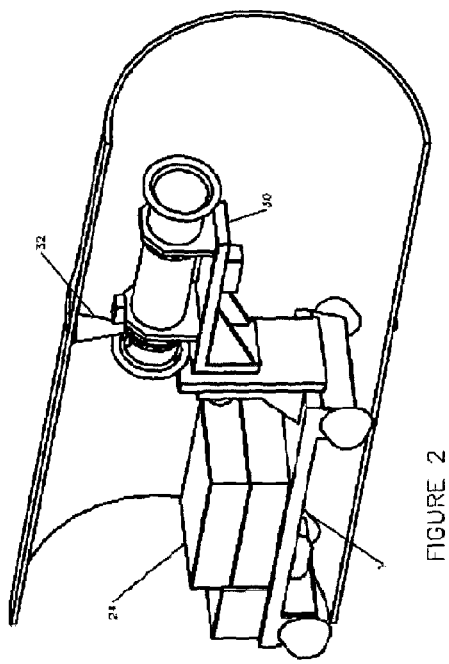
FIG. 2 shows a perspective view of the same pipeline.

The apparatus comprises a conventional crawler chassis 1 as shown in FIGS. 1 and 2 of the type used in prior art systems. This consists of a main chassis body, motor/gearbox drives 22 and drive wheels 20 at the front and back, and a battery box 24 for powering the x-ray source and the motors. The crawler is controlled by an electrical control panel that contains the x-ray controller, programmable logic controller (PLC), motor drives and interfaces.

The chassis front differs from conventional designs in that it includes a strong mounting point for an offset rotate mechanism. This mechanism, by way of example, comprises a rotate gear motor 2 supported in a strong frame 3 securely fixed to the crawler chassis. The gear motor shaft is fixed to a rotatable member or disk 4.

The rotatable member 4 has an offset mounted support cradle 30 for carrying an x-ray source 5. This support cradle also carries an inclinometer 6 and a gamma ray detector 7. A height adjustment device built into the frame 3 enables the position of the rotatable member relative to the axis of rotation of the motor 2, about which it is turned, to be moved, thereby moving the support cradle 30 radially inwards and outwards in the pipe to enable the position of the x-ray source in relation to the inside pipe wall to be adjusted for different pipe diameters and different inner pipe wall stand-offs required to achieve desired radiographic performance criteria.

The proposed inspection cycle is as follows: —

The x-ray crawler is signalled to traverse forward along the inside of a pipe by a conventional gamma signalling device 9, operated external to the pipe or by other means such as, but not limited to, radio, magnetic or ultrasound.

During the crawler's movement forward towards a weld to be inspected, an inclinometer 6 constantly adjusts the x-ray tube radial orientation such that its beam output window is always orientated in the same direction. By example this could be towards the top of pipe position. This technique also ensures that the gamma ray detector 7 is in a suitable position such as to be able to detect the external gamma signalling device 9.

By way of example, FIG. 1 shows the gamma signalling device 9 at the top of the pipe. As the x-ray crawler approaches the gamma signalling device 9 the gamma ray detector 7 identifies the peak signals from two individual and separated detection devices placed inside the gamma ray detector 7 at the housing front and rear. A programmable logic controller (PLC) uses these signals to slowly position the crawler correctly by moving the drive wheels in both forward and reverse directions to position both gamma ray detectors directly under the beam emitted from the external gamma signalling device 9. This position is attained when the signals at each detection device are the same. The gamma signalling device 9 position, thus selected, places the directional x-ray beam center in such a position as to penetrate the pipe wall at the center of the weld, when the gamma ray detectors are so positioned. This arises because the gamma rays pass through the pipeline material, which should be substantially consistent in the transmission of gamma rays. Therefore, the intensity of the rays will slope off evenly in each side of the device 9, and the lateral displacement of the gamma signalling device in relation to the x-ray source and detector is substantially the same as its displacement in relation to the weld to be inspected.

Figure 3:
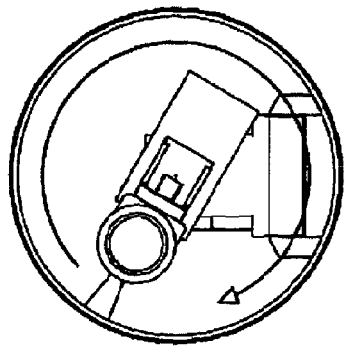
FIG. 3 shows an end view into the pipeline with the crawler head in different positions.
Figure 3:
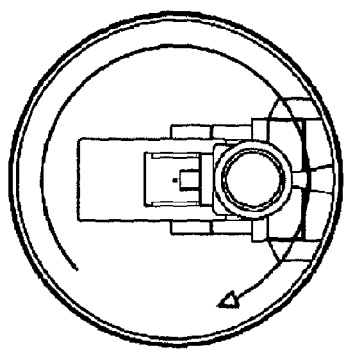
Figure 3:
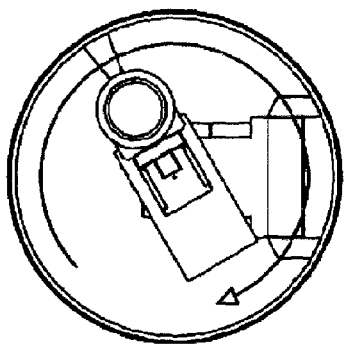
Figure 3:
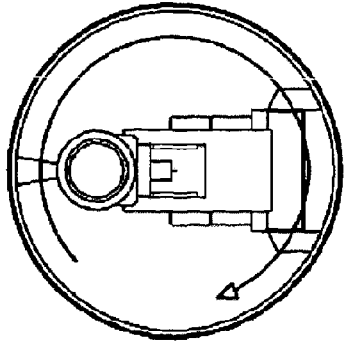

Using a method similar to that used with conventional pipeline inspection, the operator removes the gamma signalling device from the pipe, and triggers an x-ray generation sequence. The operator moves away from the pipe to a safe distance. However, unlike conventional inspection the following sequence now takes place:—The directional x-ray source 5 emits x-rays at a pre-set voltage, current and time direction after a pre-warning safety period. The RTR Detection System 10, which, for example, is mounted on a steel band 11 and driven around the pipe by a rack/pinion system 12. On detection of the x-ray flux, the RTR Detection System 10 enters a 'beam centre search mode' to position the detector directly into the position of maximum x-ray flux by moving in both clockwise and counter clockwise directions around the pipe circumference and sampling the strength of the x-rays detected. Once the beam edge positions have been detected where the detected x-ray flux goes beneath a threshold level, the detector moves to a rotational position substantially midway between these points. Because of the high x-ray flux provided by the directional x-ray source, this operation only takes a few seconds to complete. After a pre-set time from the start of x-ray generation both the x-ray source 5 and the real-time x-ray detector 10 then start to rotate at a pre-determined fixed rotational speed together around the pipe. The detector samples the detected x-rays at a plurality of sampling points around the weld. This is a design variable and is dependent on the x-ray source, the RTR device and the pipeline diameter. FIG. 3 a), b), c) and d) show the crawler with the x-ray source in different rotational positions.

The sampled data from the RTR detection may overlap and can therefore be accumulated to reduce the effects of noise. Alternatively they may not overlap. Whichever is selected, the end result is a linear profile of the penetration of x-ray flux through the weld with positions around the weld.

The combination of the inclinometer 6 for x-ray tube rotational positioning, the gamma ray detection 7 & 8 methodology and the RTR detector beam search mode ensures that both the x-ray source and RTR detector are accurately aligned to start the orbit of the pipe weld in synchronism.

This operation continues until the x-ray source and x-ray detector have orbited 360° around the pipe weld plus a small overlap. X-rays then automatically switch off when the pre-set exposure time has been reached. The operator then signals the crawler 1 using the gamma signalling device 9 to move to the next pipe weld using the gamma signalling device. At this point the RTR detector and drive mechanism may be removed from the pipe. The inspection process is repeated on the next and further welds as required. Preferably the speed of rotation is proportional to pipeline diameter.

Preferably the x-ray detector may be based on a highly customised version of an existing product used in dentistry and designed specifically for low dose, high speed panoramic x-ray. This commercial product scans a patient's jaw at high speed using a multiple line charge coupled device (CCD) which can either directly or indirectly convert low energy x-rays to an electronic signal.

By way of example one commercially available system is made up of a 3072×128 element CCD covering 150 mm width. The scan speed of the mechanism that orbits the patient's jaw is linked to the charge transfer rate from line to line on the CCD, resulting in a single output signal row with 128 times the amplitude of a single row of detectors. This type of detector is commonly called a 'time division integration' device.

In use the CCD moves around its scanning arc in a direction perpendicular to its 128 rows of CCD elements. Each element is, for example 50 microns in diameter. Charge from the elements in each row is read in a first scan and stored in respective ones of a plurality of registers, one register for each row, and each register including a storage element for each CCD element.

The CCD then advances and a second scan is performed when it has advanced a distance substantially equal to one row of CCD elements (in this case 50 microns). Charge from the elements in each row is read in the second scan. The charge is added to charge already stored for the respective row position in relation to the article being scanned. That is to say, on the first scan the leading row of CCD elements will have its charge stored in a first register, the second row in a second register, and so on. On the second scan, the leading row of CCD elements will have its charge stored in a new register. The second row of CCD elements will have its charge added to the charge in the first register as it is now detecting in the same position as the first register was on the first scan. This process of stepping through registers and adding charge to each one each time the CCD elements have moved by one row for a further scan continues until charge from the final row of CCD elements has been written to the first register. When this has happened, data from the first register can be sent to a digitizer and serial communication converter.

After the next scan the register corresponding to the second position of the first row of the CCD elements will be finished accumulating charge and can be sent to the digitizer. This process continues for the whole of the item being scanned. Thus, for each position on the scan, the charge from 128 rows of CCD elements is accumulated into a single register, for each position on the scan, thereby producing a signal where only significant variations will be masked by noise.

The overall system used by the detector described in this embodiment uses the same principles as the commercial dental product described above, but has been adapted for use with weld inspection. However, other detection systems may be used with embodiments of the invention as will be apparent to those skilled in the art.

The proposed system has two further novel features to increase radiation safety and reduce the required personnel exclusion barrier distances. Firstly the x-ray source 5 emitted beam is a highly collimated 'fan' beam 32 to cover the RTR detector input window with only a small overlap. Secondly a radiation absorbing shield 14 is attached to the RTR detector window to attenuate the entire primary beam from the x-ray source 5 such that the only x-rays present at the pipe outer surface are lower level scattered radiation.

Figure 4:
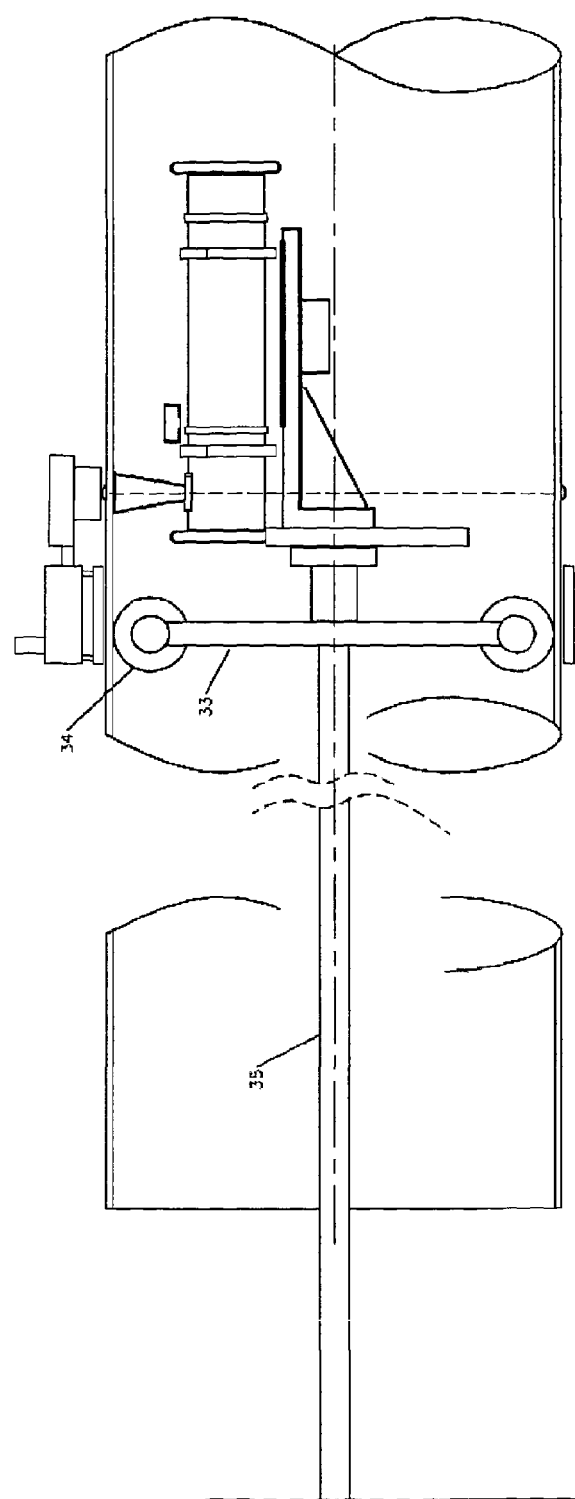
FIG. 4 shows the invention in a pipe mill or pipe yard where two or three lengths of pipe are often jointed together prior to transport to the pipeline under construction.

By way of example FIG. 4 shows another application of the invention in pipe mills that join two or three pipes together, often referred to 'double jointing' and 'triple jointing' respectfully. The radiographic inspection of these girth welds could be carried out by using the invention in full or by mounting the rotating section of the invention, or a similar configuration onto a boom arm or other load supporting device as shown in FIG. 4. This boom or arm 35 carrying the rotating sections could then be inserted into the pipeline, correctly positioned for rotation of the x-ray source a fixed distance from the inner pipeline surface using, for example, a support 'spider' 33 and supporting wheels 34, and a similar x-ray detector system positioned externally. The boom arm or other load supporting device can be positioned manually or by using a motorised system.

The invention claimed is:

1. An x-ray inspection apparatus for inspection of pipeline girth welds in a pipeline having a pipeline wall and comprising a first pipeline section and a second pipeline section, wherein the first pipeline section has an open end and is welded to the second pipeline section by one of said pipeline girth welds;
   the apparatus comprising:
   a) a directional x-ray source, wherein the directional x-ray source is radially movable within the pipeline to a desired distance from the pipeline wall,
   b) means for inserting the directional x-ray source into the open end of the first pipeline section,
   c) means for alignment of a rotational direction of the x-ray source,
   d) means for alignment of the directional x-ray source with an external x-ray detector,
   e) means for rotating the directional x-ray source and the external x-ray detector through 360° substantially co-axially with the pipeline section within which the x-ray source is positioned and substantially in synchronism with each other,
   f) means for sampling data detected by the x-ray detector, wherein the means for alignment of the directional x-ray source with the external x-ray detector comprises means for rotating the directional x-ray source in clockwise and anti-clockwise directions, and means for determining when the intensity of x-rays detected by the x-ray detector cross a threshold in each direction, such that a rotational position of the x-ray source can be positioned substantially equidistant from the two thresholds.

2. An x-ray inspection apparatus according to claim 1, wherein the directional x-ray source is rotatable at said desired distance from the pipeline wall.

3. An x-ray inspection apparatus for inspection of pipeline girth welds in a pipeline having a pipeline wall and comprising a first pipeline section and a second pipeline section, wherein the first pipeline section has an open end and is welded to the second pipeline section by one of said pipeline girth welds:
   the apparatus comprising:
   a) a directional x-ray source,
   b) means for inserting the directional x-ray source into the open end of the first pipeline section,
   c) means for alignment of a rotational direction of the x-ray source,
   d) means for alignment of the directional x-ray source with an external x-ray detector,
   e) means for rotating the directional x-ray source and the external x-ray detector through 360° substantially co-axially with the pipeline section within which the x-ray source is positioned and substantially in synchronism with each other,
   f) means for sampling data detected by the x-ray detector,
   wherein the means for alignment of the directional x-ray source with the external x-ray detector comprises means for rotating the directional x-ray source in clockwise and anti-clockwise directions, and means for determining when the intensity of x-rays detected by the x-ray detector cross a threshold in each direction, such that a rotational position of the x-ray source can be positioned substantially equidistant from the two; and
   wherein the means for alignment of the x-ray source with the x-ray detector comprises a gamma ray source mounted externally to the pipeline and a gamma ray detector mounted on the directional x-ray source.

4. An x-ray inspection apparatus according to claim 1, wherein the means for inserting the directional x-ray source into the open end of the first pipeline section comprises a crawler to travel along the inside of the pipeline section.

5. An x-ray inspection apparatus according to claim 1, wherein the means for inserting the directional x-ray source into the open end of the first pipeline section comprises a load supporting arm insertable into the pipeline section.

6. An x-ray inspection apparatus according to claim 5, wherein the load supporting arm is mounted on a support spider which moves inside the pipeline on supporting wheels.

7. An x-ray inspection apparatus according to claim 1, further comprising a rotatable member having an offset mounted support cradle, wherein the support cradle is radially movable and wherein the directional x-ray source is carried on the support cradle.

8. An x-ray inspection apparatus according to claim 7, further comprising a rotate gear motor with a gear motor shaft, the gear motor shaft being fixed to the rotatable member.

9. An x-ray inspection apparatus according to claim 4, wherein the crawler comprises a chassis on which an offset rotate mechanism is mounted.

10. An x-ray inspection apparatus according to claim 9, wherein the offset rotate mechanism comprises:
    (a) a rotate gear motor having a gear motor shaft;
    (b) a frame fixed to the chassis, wherein the rotate gear motor is supported in the frame;
    (c) a rotatable member to which the gear motor shaft is fixed.

11. An x-ray inspection apparatus according to claim 10, wherein the rotatable member has an offset mounted support cradle on which the x-ray source is supported.

12. An x-ray inspection apparatus according to claim 11, wherein a position of the rotatable member is movable relative to an axis of rotation of the rotate gear motor, so as to move the offset mounted support cradle radially inwards and outwards.

13. An x-ray inspection apparatus according to claim 12, further comprising a height adjustment device for moving the rotatable member.

14. An x-ray inspection apparatus according to claim 1, wherein said means for alignment of the rotational direction of the x-ray source comprises an inclinometer.

15. An x-ray inspection apparatus according to claim 11, wherein said means for alignment of the rotational direction of the x-ray source comprises an inclinometer, and wherein the inclinometer is carried by the support cradle.

16. An x-ray inspection apparatus according to claim 3, wherein the gamma ray source is mounted on an outer surface of the pipeline wall, wherein the gamma ray detector has a housing with a front and a rear which are axially spaced apart from one another, and wherein the gamma ray detector comprises two individual and separated detection devices located inside the gamma ray detector at the housing front and rear.

17. An x-ray inspection apparatus according to claim 16, wherein the gamma ray detector is adapted to identify peak signals from the two detection devices.

18. An x-ray inspection apparatus according to claim 1, wherein the means for rotating the external x-ray detector comprises a steel band on an outer surface of the pipeline wall, and a rack and pinion system for driving the external x-ray detector around the outer surface of the pipeline wall.

19. An x-ray inspection apparatus according to claim 1, wherein the external x-ray detector comprises a multiple line charge coupled device (CCD).

20. An x-ray inspection apparatus according to claim 1, wherein the directional x-ray source is adapted to emit a collimated fan beam and the external x-ray detector has an input window for receiving the collimated fan beam.

21. An x-ray inspection apparatus according to claim 20, wherein a radiation absorbing shield is attached to the input window of the external x-ray detector.

22. An x-ray inspection apparatus according to claim 1, wherein the means for inserting the directional x-ray source into the open end of the first pipeline section comprises a crawler to travel along the inside of the pipeline section.

23. An x-ray inspection apparatus according to claim 22, wherein the means for alignment of the x-ray source with the x-ray detector comprises a gamma ray source mounted externally to the pipeline and a gamma ray detector mounted on the crawler.

* * * * *